United States Patent [19]
Bokros

[11] Patent Number: 5,123,920
[45] Date of Patent: Jun. 23, 1992

[54] PROSTHETIC HEART VALVE

[75] Inventor: Jack C. Bokros, Austin, Tex.

[73] Assignee: Onx, Inc., Austin, Tex.

[21] Appl. No.: 585,246

[22] Filed: Sep. 19, 1990

Related U.S. Application Data

[63] Continuation-in-part of Ser. No. 537,352, Jun. 13, 1990, abandoned, which is a continuation-in-part of Ser. No. 419,288, Oct. 10, 1989.

[51] Int. Cl.⁵ ............................................... A61F 2/24
[52] U.S. Cl. ...................................................... 623/2
[58] Field of Search ................ 623/2; 137/512.1, 527.8

[56] References Cited

U.S. PATENT DOCUMENTS 4,159,543  7/1979  Carpentier .............................. 623/2
4,328,592  5/1982  Klawitter ................................ 623/1
4,892,540  1/1990  Vallana ................................... 623/2

Primary Examiner—David Isabella
Attorney, Agent, or Firm—Fitch, Even, Tabin & Flannery

[57] ABSTRACT

A bi-leaflet heart valve having an improved hinge arrangement that allows the valve to respond quickly to flow reversals and minimizes fluttering of the leaflets in the open position. A pair of leaflets are slidably and pivotally mounted in a heart valve body for movement between closed and open positions. Notches in the leaflets matingly engage complementary surfaces on pivot projections extending inward from the valve body sidewall. Downstream stops interengage with complementary surfaces on the leaflets to cushion the final opening movement and reduce wear in critical locations to improve operating characteristics.

15 Claims, 4 Drawing Sheets

PROSTHETIC HEART VALVE

This application is a continuation-in-part of application Ser. No. 07/537,352 filed Jun. 13, 1990, now abandoned, which is a continuation-in-part of application Ser. No. 07/419,288 filed Oct. 10, 1989 currently copending.

The present invention pertains to heart valve prostheses and in particular, to prosthetic heart valves using pivotable valve members, including bi-leaflet valves.

BACKGROUND OF THE INVENTION

Various types of heart valve prostheses have been developed which operate hemodynamically as a result of the pumping action of the heart. Among the types of heart valves which have been developed are valves having single occluders which pivot along an eccentric axis to open and close the heart valves, such as that described in U.S. Pat. Nos. 4,011,601, 4,423,525 and 4,425,670, and bi-leaflet heart valves, such as those described in U.S. Pat. Nos. 4,484,365 and 4,535,484. The above-mentioned patents illustrate various arrangements for pivotally connecting the valve members or occluders to a valve body and disclose occluders of a variety of shapes. However, most of these designs have never become commercial because of some shortcoming, and the need continues for improved prosthetic heart valves for permanent implantation into the human heart.

In its open position, a prosthetic valve should provide a passageway which is large and which has good flow characteristics so that blood flows freely therethrough without adverse boundary layer separation and with a minimum of drag. The heart valve should be rapidly responsive to blood flow to quickly open during the pumping stroke of the heart and to close quickly when the heart relaxes to prevent substantial regurgitation of the blood. The opening and closing of the valve should be sufficiently soft so that the patient is not disturbed by the sounds produced. The heart valve should be made of biocompatible and thromboresistant materials, such as pyrolytic carbon which is preferred, and in this regard, it is important that all surfaces be well washed by blood to prevent stagnation which might lead to eventual clotting. Furthermore, the action of the valve should be such that it does not cause hemolysis (breaking of blood cells).

Heart valves must be constructed to withstand countless numbers of openings and closings, and wear of the interacting heart valve components thus becomes important. Avoidance of excessive wear at the points which define the pivot axes of the heart valve occluders is of particular importance, and U.S. Pat. No. 4,443,894, issued Apr. 24, 1984, addressed this problem. In the bi-leaflet valve construction shown in that patent, the mounting arrangement was designed so that, in moving toward the closed position, each spherical sector which defined the pivot axis initially moved to the end of a dogleg slot; then, as a part of the seating of the arcuate edges of the leaflets against a sealing lip or seat 26, the spherical sectors are withdrawn slightly from the dead end position. However, not only was such a construction restricted to the closing movement of a pair of valve leaflets, but it was essentially restricted to a construction closely resembling that illustrated. As a result, there was felt to be a continuing need to improve designs to combat wear in heart valves utilizing various types of pivoting occluders.

SUMMARY OF THE INVENTION

The present invention provides heart valves, particularly valves of a bi-leaflet design, having the aforementioned desirable characteristics wherein a mounting arrangement is provided between the valve body and a pivoting occluder where there is sliding engagement between the pivoting occluder and an open-position stop that cushions the final movement of the occluder to thereby soften its arrival at the full-open position and, at the same time, break contact between the interengaging components that define the axis of pivotal rotation.

This arrangement is considered to be particularly useful in combination with an interengaging pivot arrangement for a pair of leaflets wherein projections extending from the interior wall of the annular valve body are formed with upstream and downstream flat surfaces and wherein the leaflets have notches formed with correspondingly disposed flat surfaces that lie in juxtaposition to the projection flat surfaces in the open position. One result of such an arrangement is to disengage the upstream flat surfaces just before the leaflets reach their fully open position, thereby reducing wear at this point and cushioning the ultimate movement. In addition, this location of the stops is effective to change the stress pattern to which the leaflets are subjected at the instant of final closing and thereby alleviate the potential fatigue of the leaflets in this general region as a result of countless openings and closings.

DETAILED DESCRIPTION OF THE PREFERRED EMBODIMENT

A heart valve, generally designated 10, of bi-leaflet construction is illustrated; however, it should be apparent to one of ordinary skill in this art that the principles of the present invention can be applied to a prosthetic heart valve having a single occluder. Heart valves embodying the present invention exhibit rapid response in both opening and closing, relatively small impact when the leaflets contact the valve body, and substantial avoidance of hemolysis or like injury to blood cells flowing through the valve.

Figure 1:
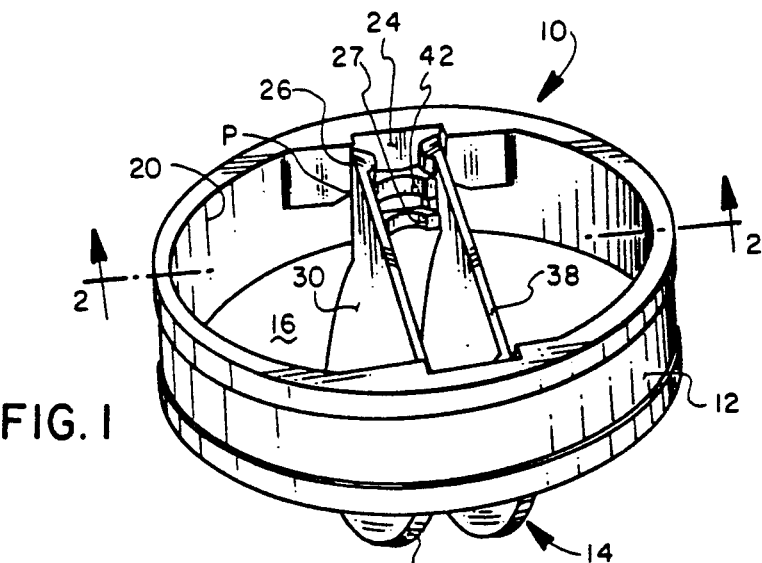
FIG. 1 is a perspective view of a bi-leaflet heart valve embodying various features of the present invention, shown in its open position.
Figure 2:
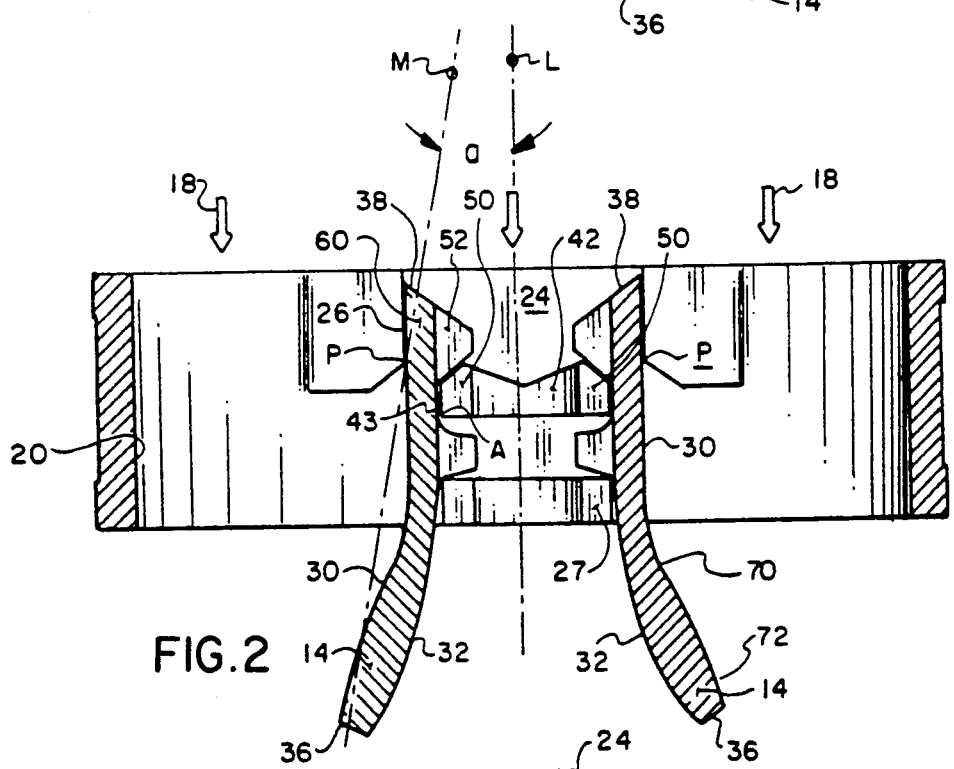
FIG. 2 is an enlarged cross-sectional view of the heart valve taken along the line 2—2 of FIG. 1, showing the valve in its open position.

The heart valve 10 includes a generally annular valve body 12 and a pair of pivoting valve occluders or leaflets 14, which open and close to control the normal flow of blood in the downstream direction of arrows 18 (see FIG. 2). Blood flows through passageway 16 which is defined by a generally cylindrical interior surface or sidewall 20 of body 12. The cylindrical surface of sidewall 20 is interrupted by a pair of diametrically opposed flat wall sections 24. Flanking each of these flat wall sections is a pair of abutments 26 which act in combination with a protrusion or ledge 27 to stop the rotation of the leaflets when the leaflets reach fully open position, as illustrated in FIGS. 1 and 2.

Figure 3:
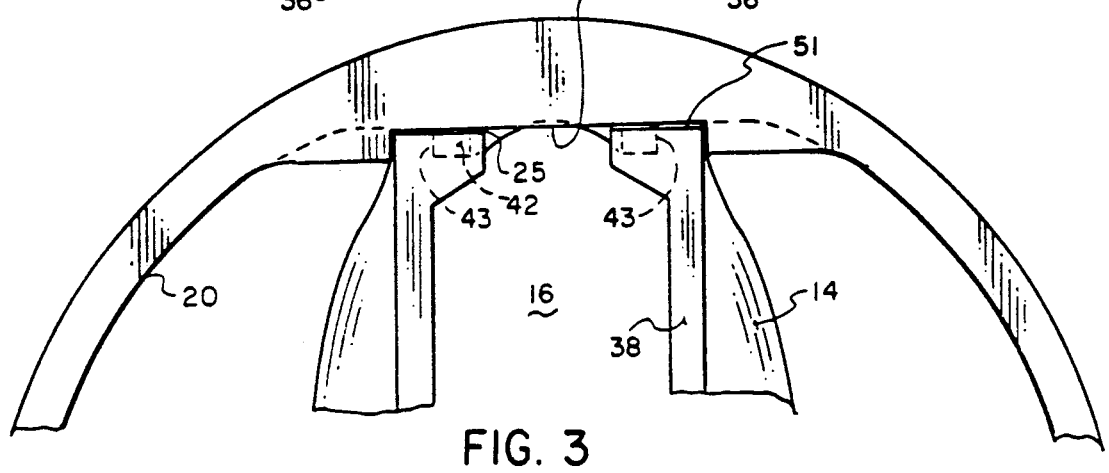
FIG. 3 is a fragmentary plan view of the bi-leaflet heart valve shown in FIG. 1, showing the valve in an open position.
Figure 11:
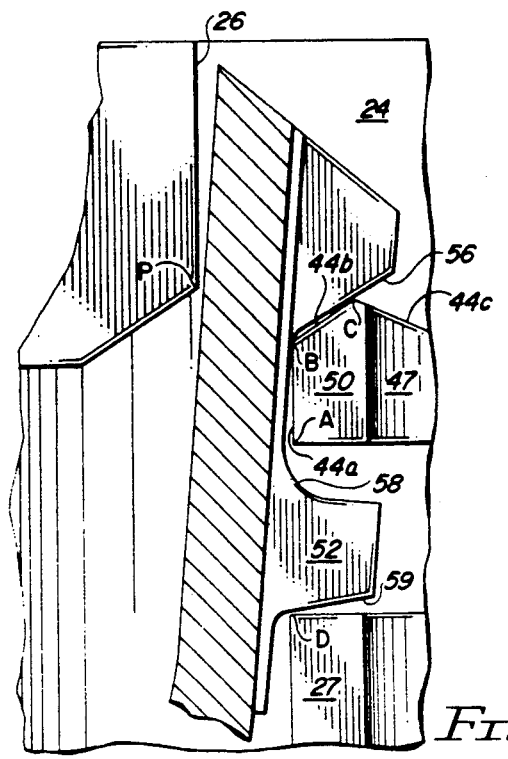
FIG. 11 is an enlarged, fragmentary, cross-sectional view showing the mating engagement between a pivot and a leaflet notch with the leaflet approaching its fully open position.
Figure 12:
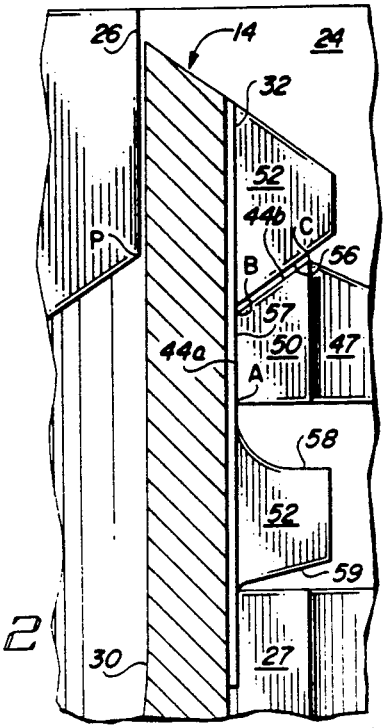
FIG. 12 is an enlarged, fragmentary, cross-sectional view similar to FIG. 11 showing the mating engagement between the pivot and the leaflet notch with the leaflet in its fully open position.

As best seen in FIGS. 1 through 3, and in FIGS. 11 and 12, diametrically opposed projections 42 extend generally perpendicularly from the flat wall sections 24; each projection 42 has a pair of oppositely facing lateral pivots 43. Each pivot 43 has three flat seating surfaces or facets 44a, 44b and 44c, each oriented from the next adjacent facet at an angle of between about 110° and about 130°, and preferably approximately 125°. In the preferred embodiment, facet 44a is oriented substantially parallel to the axis of blood flow, with the other two facets 44b and 44c lying upstream thereof (see FIG. 11). The projections 42 have center sections 47 which are recessed so as to minimize the transverse surface area in the path of blood flow through the passageway 16 and inward facing surfaces 50 of the projections 42 are flat and generally parallel to the flat wall section 24 of the valve body. The three seating surfaces 44a, 44b, and 44c are perpendicular to the flat wall section 24 of the valve body and to the parallel flat end portion 50. These pivots matingly engage with notches 53 formed in the leaflets 14.

The leaflets 14 each have an upstream or inflow surface 30 and an opposed downstream or outflow surface 32. The cross-sectional view of FIG. 2, which is taken along the leaflet centerline perpendicular to its axis of rotation, shows that the thickness of the leaflets varies considerably from one end of the leaflet to the other. This design reduces impedance of the leaflets to blood flow therethrough as a result of the composite curvature of the leaflets. As described in the U.S. Pat. Application Ser. No. 392,745, filed Aug. 11, 1989, the disclosure of which is incorporated herein by reference, the rapid response of the leaflets to reversals in the direction of blood flow is attributable in part to the hinge mechanism.

The inflow surface 30 of each leaflet has a concave region 70 of two-dimensional curvature resembling a curved sheet. As used herein, a two-dimensional curved surface is one which is made up of a plurality of straight lines that extend laterally completely across the leaflet arranged to define a curved surface, which lines are all parallel to one another. In other words, planes parallel to the pivot axis will cut the two-dimensional inflow surface along straight lines, whereas planes perpendicular to the pivot axis will cut the two-dimensional inflow surface along a line having the same curvature regardless of whether the plane is the centerline plane or laterally offset therefrom. The leaflet inflow surfaces 30 include a convex region 72, also of generally two-dimensional curvature, downstream of the concave region 70. The convex region 72 when cut by a plane perpendicular to the pivot axis may exhibit a curvature resembling a paraboloid, an ellipsoid or some other smooth arcuate shape. Preferably, the various portions of the major leaflet surfaces are blended so as to have smooth transitions from one to another.

The outflow surface 32 of each leaflet 14 includes a convex surface region that is preferably at least coextensive with the opposing inflow concave region 70 and inflow convex region 72. The leaflets have a maximum thickness where the convex surfaces oppose each other. Each leaflet has a major arcuate peripheral surface 36, which lies in juxtaposition with the valve body sidewall in the closed position.

The leaflets 14 have, in addition to the major arcuate peripheral surface 36 which is located at the trailing edge of a fully opened leaflet, a minor flat mating surface 38 that is located at the opposite, leading end of the leaflet. The flat minor surface 38 is oriented to mate or lie in juxtaposition with the corresponding surface of the opposing leaflet. This minor surface 38 is oriented at an obtuse angle with the flat section of the outflow surface 32 of the leaflet 14 which angle is chosen such that the two minor surfaces 38 abut along substantially their entire lengths when the valve is in the closed position.

Figure 4:
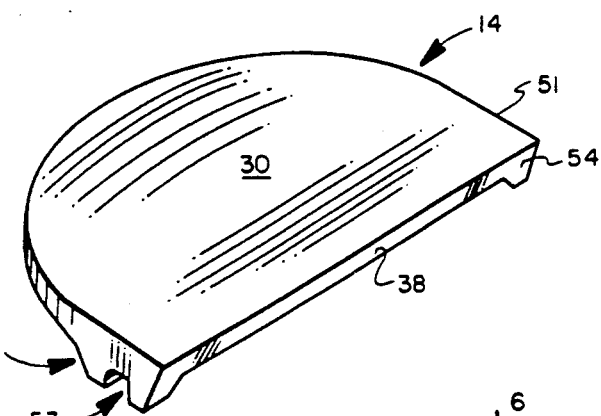
FIG. 4 is a perspective view of a leaflet from the valve shown in FIG. 1.
Figure 5:
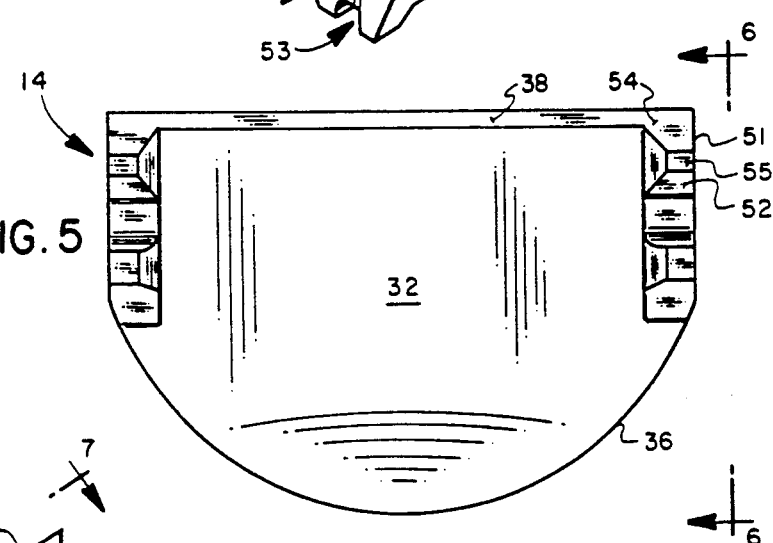
FIG. 5 is a an enlarged elevational view of the leaflet shown in FIG. 4 showing the downstream or backflow surface.
Figure 6:
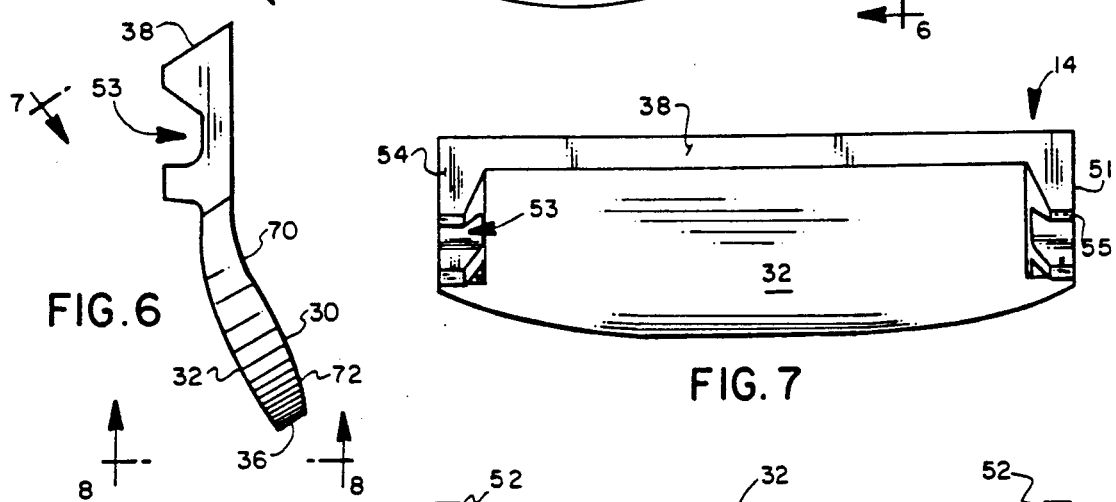
FIG. 6 is a side elevational view of the leaflet of FIG. 4, looking along line 6—6 of FIG. 5.
Figure 7:
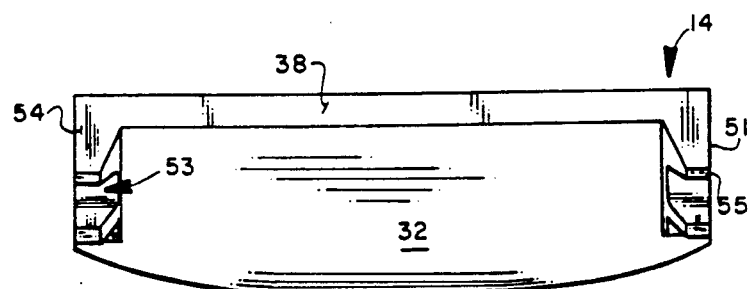
FIG. 7 is an elevational view of a leaflet, taken looking along line 7—7 of FIG. 6.
Figure 8:
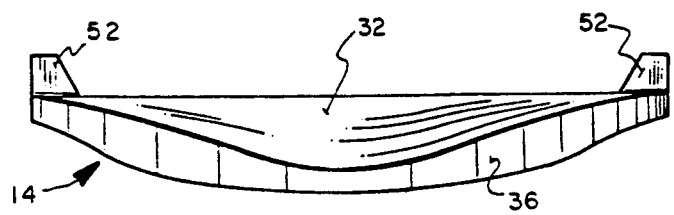
FIG. 8 is an elevational view of a leaflet, taken looking along line 8—8 of FIG. 6.

Referring to FIGS. 4 and 5, leaflets 14 each include a pair of opposed, lateral surface sections 51 which are interposed between the major arcuate surface 36 and the minor mating surface 38. These lateral surface sections 51 of the leaflets are preferably flat, and the leaflets are proportioned so as to provide a minimal clearance 25 with the flat wall sections 24 of the valve body 12 (See FIG. 3) during pivoting movement of the leaflets 14.

Figure 9:
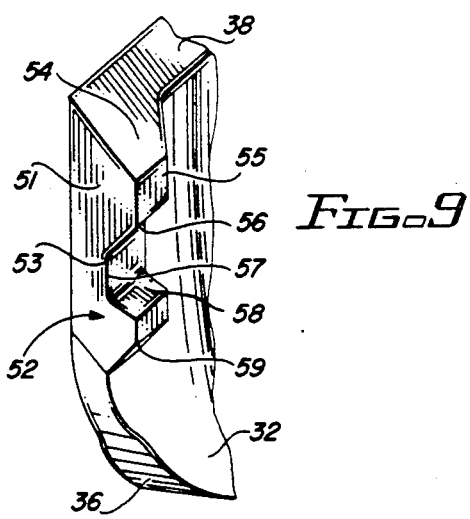
FIG. 9 is an enlarged fragmentary perspective view of the leaflet of FIG. 4, particularly illustrating the notch in the extension of the leaflet.

As best seen in FIG. 9, extending from the outflow surface 32, adjacent both lateral surface sections 51, are extensions 52 which each have an upstream end surface 54, a bottom surface 55, and a downstream end surface 59. The upstream end surface 54 of the extension 52 is formed at an obtuse angle with the flat section of the backflow surface 32 of the leaflet 14 so as to preferably form a continuous, smooth surface with the flat minor mating surface 38. The opposed minor mating surfaces 38 and the extensions 52 provide combined surfaces of substantial thickness which result in several advantages on valve closing. For example, the increased surface area of the mating surfaces 38 distributes forces over a greater area upon contact between mating surfaces, thus reducing stress and wear on the leaflets. Also, with the valve in a fully closed position, the increased surface area lengthens the region of abutment between the leaflet mating surfaces and deters leakage.

Notches 53 are formed in each extension 52 and have two flat or straight surfaces 56 and 57 oriented so as to mate with the facets 44a and 44b, e.g., at an angle of about 125° with respect to each other, and a third, curved surface 58. In the preferred embodiment, the first straight surface 57 is substantially parallel and preferably coplanar with the flat section of the inflow surface 32 of the leaflet; the second straight surface 56 is adjacent and on the upstream side thereof (with the leaflet in the open position). The curved surface 58 is adjacent and on the downstream side of the first straight portion 57, and it extends smoothly therefrom, being preferably tangential thereto. The downstream surfaces 59 of the extensions 52 are oblique in an upstream direction to the flat outflow section of the leaflet 14 being formed at an angle between about 100° and about 120°; they are accordingly at an angle of between about 60° and about 80° to the centerline plane through the valve body. By the centerline plane is meant the plane which is perpendicular to the flat wall sections 24 and contains the centerline through the valve passageway.

Referring to FIG. 2, the extensions 52 provide additional structural support to the upstream or leading end, otherwise flat, portions 60 of the leaflets 14 which carry the stress of halting leaflet movement, particularly in the open position. As described in U.S. Pat. Application Ser. No. 4,872,875, the flat leading end portions 60 of the leaflets 14, in the central regions between the extensions 52, have a significantly constant thickness, which is generally significantly less than the downstream thickness, as is apparent from the cross-sectional views of FIGS. 2 and 10. Extensions 52 are preferably formed integral with the leaflets 14 so that the leaflets have an increased thickness at the locations where stresses are encountered.

The leaflets 14 are installed in the valve body 12 by squeezing the body at diametrically opposed locations, i.e. those where the valve body is cut by the reference line 2—2 in FIG. 1. This causes the body to bulge outward at the diametrically opposed flat wall sections 24, thus allowing the leaflets 14 to be fitted into the passageway 16 of the valve body. The extensions 52 of the leaflets fit between the pivots 43 and the abutments 26, with the pivots 43 being received in the notches 53. The squeezing force is then removed allowing the flat wall sections 24 to return to their original spacing. Referring to FIG. 3, the lateral surfaces 51 and extensions 52 of the leaflets 14 are preferably dimensioned to provide a small clearance 25 with the corresponding adjacent flat wall sections 24 of valve body 12. The notches 53 and the pivots 43 define the pivot axes about which the leaflets slidably and pivotally rotate between open and closed positions. This is discussed further below in relation to the operation of the valve.

The leaflets are slidably and pivotally mounted for rotation between closed and open positions, and it is generally preferred that the opening, and particularly the closing, motions of the leaflets be made as rapid as possible. However, the end points of the termination of movement of the leaflets should be well defined and designed to reduce noise and leaflet wear. For example, the leaflets should not bounce back when contacting seating surfaces defining the end points of their travel, nor should the major peripheral surfaces 36 extend beyond the valve body 12 when in a closed position.

Figure 10:
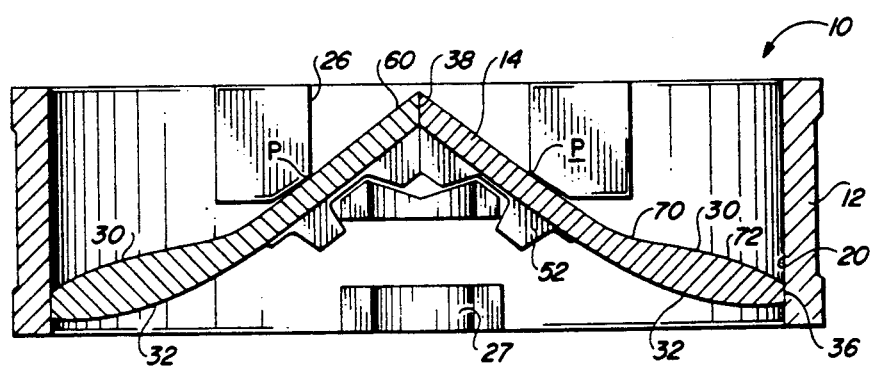
FIG. 10 is a cross-sectional view of the heart valve of FIG. 1 in its closed position.

FIG. 2 shows the inflow surfaces 30 of leaflets 14 lying generally adjacent the relatively flat, vertically oriented surfaces of the abutments 26 which, along with downstream stops 27, define the extent of opening of the leaflets, thus fixing one end of their travel. The stops 27 extend inwardly from the flat wall sections 24 at locations downstream of the pivot projections; they are positioned so as to engage the oblique surface 59 of the extensions as explained hereinafter. Similar to the pivot projections, the centers of the stops 27 are preferably recessed to minimize the transverse surface area exposed to, and impeding, the flow of blood through the passageway 16. Employing stops 27 in addition to abutments 26 to halt rotation of the leaflets 14 results in less wear on the pivots and the interengaging surfaces of the notches because of the manner in which leaflet impact is cushioned at the end point of such movement, as explained hereinafter. On the other hand, the final closed position of the leaflets is defined by the abutting, minor, mating surfaces 38 of the leaflets, and/or the contact between the major, arcuate surfaces 36 and the interior surface or sidewall 20 of the valve body 12 (which may have formed therein a seating region), and contact along the inclined surface of the abutment 26, likely at edge P (FIG. 10).

As best seen in FIG. 2, abutments 26 and stops 27, in combination with the flat seating surfaces 44a and 44b of the pivots 43, define the fully open position of leaflets 14. In the preferred embodiment, the mating flat surfaces 38 do not extend beyond the valve body when the leaflets are in their open position. It is generally desirable to orient the fully open leaflets for minimum obstruction of the downstream flow through the valve body passageway 16. As can be seen in FIG. 2, the flat portions 60 of the leaflets 14 are oriented essentially parallel to the direction of blood flow, generally indicated by arrows 18.

The leaflets 14 undergo controlled angular displacement between their fully closed and fully open positions. With reference to FIG. 2, the angle of opening (i.e. the angular orientation of the leaflets when in the open position), identified by the reference letter a, has a value ranging between about 1 and about 20°. Preferably, this angle of opening of the leaflets is between about 5° and about 20°, and most preferably, is between about 7° and about 13°. As used herein, the term "angle of opening" is defined as the angle between two planes which are both perpendicular to the flat surfaces 24, one of which (see reference character M) longitudinally bisects the minor mating surface 38 and also contains the midpoint of the major arcuate surface 36 and the other of which contains the centerline of the valve body passageway (see reference character L).

The centerline L of the passageway 16 through the valve body 10 lies midway between the pivot axes, and in the fully open position, the outflow surfaces 32 of the leaflets lie facing each other on opposite sides of the centerline L, with the portions of the leaflets 14 within the valve body 12 extending generally parallel to the central axis L. In the fully closed position as shown in FIG. 10, the minor, mating surfaces 38 of the leaflets 14 abut each other, preferably along their entire flat surfaces. No matter which opening angle a is chosen, it is generally preferred that the leaflets 14 are not brought into a generally straight-line relationship when fully closed, in order to avoid a risk of wedging of the leaflets. Instead, the leaflets 14 should have an obtuse angular relation to each other, preferably less than about 150°, as shown in FIG. 10.

Operation of the heart valve 10 will now be described as the leaflets begin movement from a fully closed position wherein the two flat surfaces 56 and 57 of each notch 53 lie in juxtaposition to the two upstream flat seating surfaces 44b and 44c of the pivot 43, there being a small clearance between these adjacent surfaces (see FIG. 10). When the cardiac cycle reverses, blood flows in the direction of the arrows 18 (FIG. 2), and in initial valve opening movement, the leaflets are displaced in the downstream direction until the flat surfaces 56 and 57 of the leaflet notches 53 are pressed against the facets 44b and 44c of the pivot projections 42. The eccentric location of the pivot axis causes a moment imbalance to develop as a result of the forces bearing against the larger portions of the inflow surfaces 30 that are located generally downstream of the pivot axes. This imbalance causes the leaflets 14 to begin to rotate about the pivots 43 in the direction of valve opening, with their minor mating surfaces 38 moving apart and approaching the abutments 26; contact is between the leaflet notch surfaces 56 and 57 and the pivots 43. The amount of force on the pivots 43 decreases as the leaflets 14 open more widely, due to reduced leaflet surface area generally transverse to the path of the blood flow. As the leaflets 14 swing toward the fully open position, the points of contact continuously change between the pivoting notches 53 with the edges B and C of the pivots 43, the effect of which continuous shifting of contact points is discussed in the aforementioned application.

As shown in FIG. 11, the relative proportioning of the notches 53 and the relative spacing between the pivots 43 and the downstream stops 27 which protrude from the interior sidewall of the valve body are such that, as the leaflets approach the fully opened position, there is engagement between the upstream edge D of the stop 27 and the oblique surface 59 of the extension 52. The contact has two effects. First, it cushions the impact between the pivoting leaflet 14 and the downstream stop 27. Second, it effects this cushioning by forcing or lifting the leaflets slightly upstream, breaking contact between the edge C and the surface 56 of the notch, and thus alleviating a point of potential wear. The lifting results in a sliding of the flat notch surface 57 generally along the edge B of the facet 44a. As a result, as can be seen in FIG. 12, when the leaflets reach the fully open position, the facet 44b is in close juxtaposition to the notch surface 56, but there is no contact therebetween. There is, however, contact between the facet 44a and the notch surface 57 and between the oblique surface 59, near its end, and the edge D of the downstream stop 27, all of which serve to eliminate flutter of the leaflets in the open position. In addition, in the fully open position, there may be contact between the flat section of the inflow surface 30 of the leaflet and the surface of the abutment 26 that lies parallel to the centerline of the valve, although there can be a slight clearance between the two surfaces, as shown in FIG. 12. The only flutter possible in this open position would be extremely slight movement for a distance equal the extent of this tolerance, and it can thus be seen that the upstream abutment 26 and the downstream stop 27 in combination with this notch arrangement create an extremely stable open position for this bi-leaflet valve.

Upon a reversal of the cardiac cycle, blood flow develops in an upstream direction, generally opposite that of the arrows 18 of FIG. 2. The force of back-flowing blood against the leaflet outflow surface 32 causes the leaflets 14 to be shifted slightly upstream, i.e. in an upward direction as depicted in FIG. 2, and to begin to pivot in a closing direction. Upon this shifting of each leaflet, there is engagement between the downstream edge labeled A on the pivot 43 and the curved notch surface 58, and there is contact between the lower edge P of the abutment 26 and the flat section of the inflow surface 30. This acts to provide an initial, rapid pivoting of the leaflet 14 in a closing direction which, in turn, exposes a greater portion of the outflow surface 32 of the leaflet to the direct force of the backflowing bloodstream. As the leaflet outflow surface 32 become more transverse to the flow of blood, the rate of closing increases.

The closing movement of the leaflets is stopped upon contact between the minor, mating edge surfaces 38 of the leaflets and/or contact of the major, arcuate surfaces 36 with the interior surface or sidewall 20 of the valve body 12 which may optionally have a seating region formed therein. Throughout much of the leaflet closing movement, there is contact between the inflow surface 30 and the edge P on abutment 26, and the leaflets come to rest in the fully closed position (FIG. 10) with the edge P on abutment 26 in contact with the inflow surface 30.

As explained in U.S. Pat. Application Ser. No. 392,745, filed Aug. 11, 1989, at the beginning of leaflet closing movement, a large closing moment is favored which causes the leaflet to respond quickly to flow reversal. However, as the closing movement continues, the instantaneous center (IC) of points on the leaflet varies because of the changing points of contact between the notches 53 and pivots 43, the result of which is a reduced impact when the leaflet arcuate surface 36 contacts the valve sidewall, compared to the impact a similar valve member would have rotating on a pivot of circular cross-section. Moreover, the contact with the edge P during closing creates frictional drag along the flat section of the inflow surface 30 which slides therealong and also reduces the impact of closing. A result of this soft closure from the effect of the changing IC and the fractional drag is a significant lessening in the "water hammer" effect that is thought to cause cavitation which can be damaging to pyrolytic carbon, a preferred material of construction of heart valve components. Likewise, during the initial opening movement of the leaflet 14, a large opening moment is favored which causes the leaflet to respond quickly to flow reversal. As the opening movement continues, the IC migrates so as to also tend to reduce impact which is further cushioned by the engagement between the oblique surface 59 and the edge D.

Heart valves 10 constructed according to the principles set forth herein provide numerous advantages, particularly from the standpoint of providing a commercially feasible embodiment that responds very quickly to the reversal of flow, yet does not unduly stress the relatively thin leaflets at the moment of impact either at the end of the opening movement or at the end of the closing movement where the propensity of creating a "water hammer" effect is greatly reduced along with the chance of cavitation erosion. This is considered quite important because of the countless openings and closings to which a heart valve will necessarily be exposed over the lifetime of the recipient, and particularly by being able to transfer the point of potential wear to locations, namely the oblique surface 59 and the edge D of the downstream stop, that are not critical to determining pivotal movement, minor amounts of wear can be tolerated without adversely affecting the performance of the valve.

Figure 13:
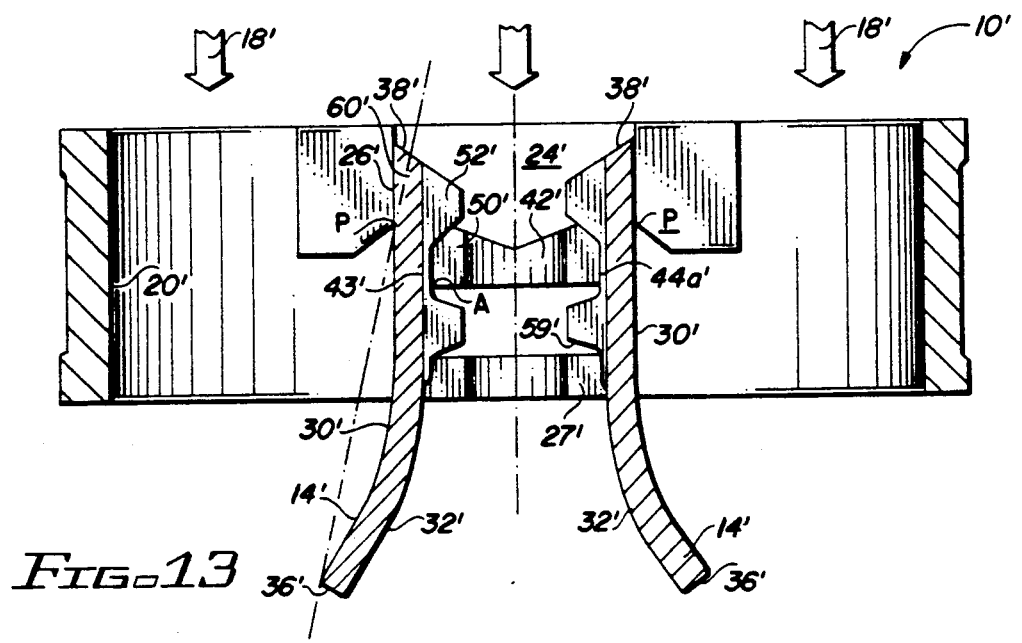
FIG. 13 is a view similar to FIG. 2 of an alternative embodiment of a heart valve embodying various features of the invention, showing the leaflets in the open position.
Figure 14:
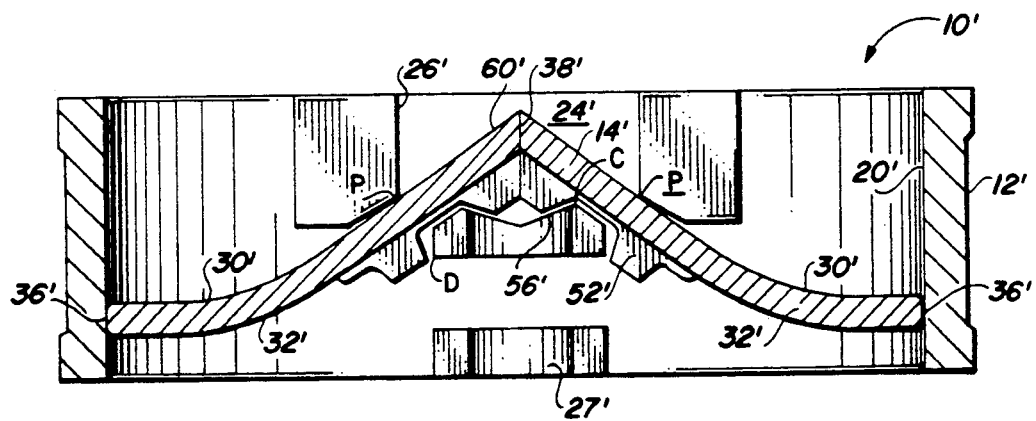
FIG. 14 is a cross-sectional view of the valve shown in FIG. 13 with the leaflets shown in the closed position.
Figure 15:
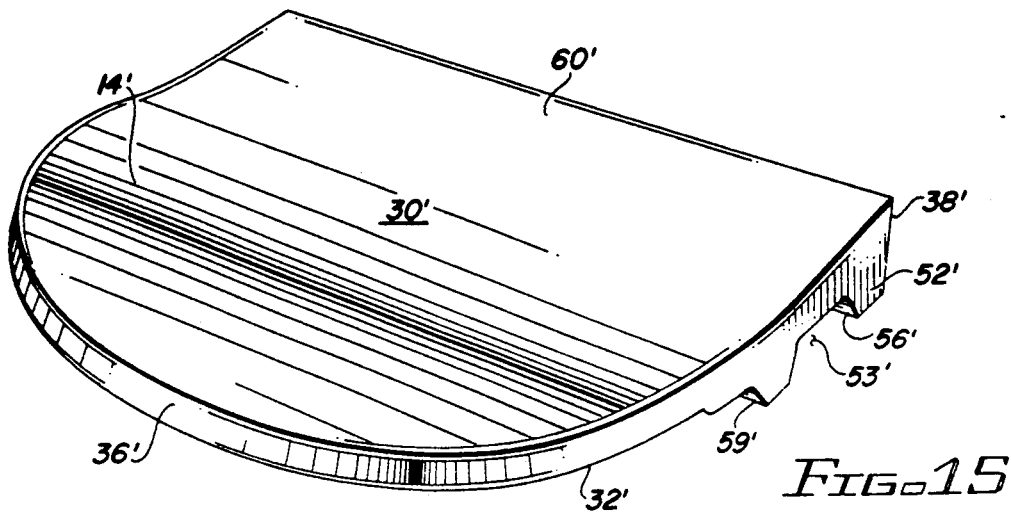
FIG. 15 is a perspective view, enlarged in size, of one of the leaflets from the valve depicted in FIGS. 13 and 14.

Although the effects and advantages set forth in the foregoing paragraph are particularly true of heart valves having the leaflet construction shown in FIGS. 1-12, substantially all of these advantages can also be obtained through the use of leaflets of simpler design, such as those shown in the alternative embodiment of a heart valve 10' illustrated in FIGS. 13-15. The alternative embodiment utilizes a valve body 12' of precisely the same construction as that described in respect of the valve 10 illustrated in FIGS. 1-12, in combination with a pair of leaflets 14'. When viewed looking at their downstream surfaces 32', the leaflets 14' appear identical to the leaflets 14 shown in FIGS. 1-12, but from a side sectional view, it is apparent that the leaflets 14' are of uniform thickness throughout with the exception of the regions where the pivot extensions 52' are located. In this respect, it can be seen that the downstream portion of each inflow surface 30' is concave and has the same curvature as the opposite convex section of the outflow surface 32'. Accordingly, the length and outline of the major peripheral surface 36' is the same as that hereinbefore described. Likewise, the flat minor mating surfaces 38' are also precisely the same as hereinbefore described.

Overall, the flat sections 60' of the leaflets 14' are essentially the same as their counterparts in the leaflets 14 with the differences being in the downstream curved portions. The extensions 52' each include a notch 53' of precisely the same construction as earlier described, and the downstream oblique surface 59' of each extension, as previously described, will during the final segment of the opening movement engage the edge D of the downstream stops 27'. As a result, the cushioning effect upon the leaflets at the end point of their opening movement occurs as hereinbefore described. More specifically, as the leaflets 14' approach their fully open position, there is engagement between the upstream edge D of the stop 27' and the oblique surface 59' which cushions the impact at the end point of the movement by forcing or lifting the leaflets slightly upstream and thereby breaking contact between the edge C and the surface 56' of the notch in the same manner as hereinbefore illustrated in respect of FIG. 12. As a result, the simplified version of the heart valve 10' achieves substantially all of the advantages of the heart valve 10 while it is considerably easier to manufacture because of its substantially uniform thickness and substantially uniform curvature throughout major portions of the leaflets 14'.

Although the present application sets forth the preferred embodiments which constitute the best mode for carrying out the invention, it should be understood that changes and modifications as would be obvious to one having the ordinary skill in this art may be made without departing from the scope of the invention which is defined in the claims appended hereto. For example, although preferably the cushioning is effected by engagement between an oblique surface on the leaflet and an edge of the stop, these could be reversed and edges on the leaflets could be positioned to engage oblique surfaces on the downstream stop. Although the valve body and the leaflets are preferably made of pyrolytic carbon or of isotropic graphite coated with pyrolytic carbon, which provides nonthrombogenic surface characteristics, other suitable materials can be employed to achieve the same mechanical advantages as set forth herein. Moreover, as indicated hereinbefore, although the preferred embodiment employs a pair of leaflets, the principles of the invention can be incorporated into known heart valves which utilize a single occluder and a downstream stop mechanism of this type.

Particular features of the invention are emphasized in the claims that follow.

What is claimed is:

1. A prosthetic heart valve which comprises
   a generally annular valve body having an interior sidewall which defines a central passageway therethrough for the passage of blood in a downstream direction, said central passageway having a centerline which extends therethrough,
   occluder means including a pair of leaflets of substantially identical design which are designed to pivot about a pair of parallel axes within said valve body, each said leaflet having an inflow surface and an outflow surface, and
   pivot means allowing said leaflets to pivot between an open position and a closed position wherein said outflow surfaces face downstream,
   each said leaflet having a protrusion which extends downstream from said outflow surface with said leaflets in the closed position,
   said pivot means including a pair of projections extending generally radially inwardly into said central passageway from said interior sidewall and a notch in said protrusion of each said leaflet for receiving said projections,
   said valve body having upstream abutments extending into said central passageway from said interior sidewall configured to engage said inflow surface and thereby serve as upstream stops, and
   said valve body further including downstream stop means which projects generally radially inward from said sidewall, downstream from said pivot projections, said downstream stop means being configured to engage said respective protrusion before said leaflets reach full open position and to cam said leaflets in an upstream direction as said leaflets reach full open position.

2. A heart valve in accordance with claim 1 wherein each of said projections and notches is formed with at least one flat surface, said flat surfaces of each of said projections and notches, respectively, being positioned such that, when said leaflets are in the open position, said flat surfaces of said projections are in juxtaposition with said flat surfaces of said notches.

3. A heart valve in accordance with claim 1 wherein each of said leaflets has a flat body section and wherein said upstream abutments and said downstream stop means are aligned such that said flat body section of said leaflet is parallel to the centerline of the central passageway.

4. A prosthetic heart valve which comprises
   a generally annular valve body having an interior sidewall which defines a central passageway therethrough for the normal passage of blood in a downstream direction, said central passageway having a centerline which extends therethrough,
   occluder means having an inflow surface and an outflow surface which is designed to pivot in said valve body to alternately permit the flow of blood therethrough in a downstream direction and block the backflow of blood, said outflow surface having an oblique surface formed thereon,
   a pivot arrangement allowing said occluder means to pivot between an open position and a closed position wherein said outflow surface faces downstream, said pivot arrangement including a pair of projections extending generally radially inwardly into said central passageway from said interior sidewall and a pair of notches in said occluder means for receiving said projections, each of said projections being formed with at least one flat surface, each of said notches having at least one flat surface, which has a downstream edge when said occluder means is in the open position, and a curved surface extending from the downstream edge of said flat surface, said respective flat surfaces being positioned such that, when said occluder means is in the open position, said one flat surface on each of said pair of projections is in juxtaposition with said one flat surface in each of said notches, whereby, upon reversal of flow of blood through said valve body, said occluder means is immediately displaced slightly upstream causing said curved notch surface to engage a downstream edge of said projection and resulting in said occluder means immediately beginning to pivot toward its closed position as said upstream displacement begins, and said valve body means being provided with stop means which also project generally radially inwardly from said interior sidewall at locations downstream from said pivot surface projections, the relative location of said stop means being such that said oblique surface formed on said outflow surface of said occluder means slidingly engages said stop means before said occluder means reaches its full open position.

5. A heart valve according to claim 4 wherein said valve body includes a pair of abutments extending generally radially inwardly from said interior sidewall, one of said abutments being spaced from each of said projections and located so that a region of each said abutment is engaged by said inflow surface of said occluder means as it pivots from the open to the closed position.

6. A heart valve according to claim 5 wherein said occluder means includes a pair of leaflets of substantially identical design which pivot about a pair of parallel axes within said valve body.

7. A heart valve according to claim 6 wherein each said leaflet h as a protrusion which extends outward from its outflow surface, said protrusion having said oblique surface formed upon a downstream-facing surface portion thereof with said leaflets in the open position, said oblique surface being located so as to slidingly engage an edge on an upstream portion of said stop means just before said leaflet reaches its fully open position.

8. A heart valve according to claim 7 wherein said oblique surface is oriented at an angle of between about 60° and about 80° to a plane including the centerline of said central passageway through said valve body when said leaflet is in the open position and wherein said stop means includes a surface generally perpendicular to said centerline which has an edge that is located so that, when it is engaged by said oblique surface of said leaflet pivoting toward the open position, said pivoting leaflet is forced slightly upstream, causing disengagement between said one flat surface of said pivot projection and said one flat notch surface before said leaflet reaches full open position.

9. A heart valve in accordance with claim 8 wherein each said leaflet has a flat body section and wherein said downstream stop means is located relative to a surface on said abutment which serves as an upstream stop means so as to align said flat body section of said leaflet so that it is substantially parallel to the centerline of the central passageway through said valve body.

10. A prosthetic heart valve which comprises a generally annular valve body having an interior sidewall which defines a central passageway therethrough for the passage of blood in a downstream direction, occluder means having an inflow surface and an outflow surface which is designed to alternately permit the flow of blood therethrough in a downstream direction and block the backflow of blood, said occluder means having protrusion means formed thereupon which extends outward from said outflow surface, a pivot arrangement allowing said occluder means to pivot between an open position and a closed position wherein said outflow surfaces faces downstream, and said valve body being provided with upstream stop means and downstream stop means which both project generally radially inwardly from said interior sidewall and define said open position of said occluder means by abutment therewith, said downstream stop means being designed and positioned to slidingly engage said protrusion means on said occluder means before said occluder means reaches said open position and thereby cushion the final movement of said occluder means in reaching said open position.

11. A heart valve according to claim 10 wherein said occluder means includes a pair of leaflets of substantially identical design which pivot about a pair of parallel axes within said valve body.

12. A heart valve according to claim 11 wherein said pivot arrangement includes a pair of projections extending generally radially inwardly into said central passageway from said interior sidewall and a pair of notches in each of said leaflets for receiving said projections, each of said pivot projections being formed with upstream and downstream flat surfaces oriented at a predetermined angle to each other and each of said notches having a flat upstream surface which has a downstream edge, with respect thereto with said occluder means in the open position, and which has a flat intermediate surface which meets said upstream surface along said downstream edge thereof, said notch flat surfaces being oriented at the same predetermined angle to each other, and said respective flat surfaces being positioned so that, when said leaflets are in the open position, said pair of flat surfaces on said projections are in juxtaposition with said flat surfaces in said notches.

13. A heart valve according to claim 12 wherein said protrusion means extends from the outflow surface of each said leaflet at locations near the lateral edges of said leaflets, said notches being formed in said protrusion means, each said protrusion means having an oblique downstream-facing surface portion formed thereon which is located so as to engage an upstream edge of said downstream stop means just before said leaflet reaches said open position.

14. A heart valve according to claim 13 wherein each said leaflet has a generally flat body section from which said protrusion means extend, said oblique surface being oriented at an angle of between about 100° and about 120° to said flat body section and wherein said downstream stop means includes a surface which is substantially perpendicular to the centerline of said central passageway and which has an edge that is located so that it engages said oblique surface as siad leaflet pivots toward said open position and causes said pivoting leaflet to be forced slightly upstream, causing disengagement between said upstream pivot projection and said upstream notch surface before the leaflet reaches said open position.

15. A heart valve in accordance with claim 14 wherein said downstream stop means is located relative to said upstream stop means so as to precisely align said flat body section of said leaflet so that it is parallel to the centerline of the flow passageway in said open position.

* * * * *

UNITED STATES PATENT AND TRADEMARK OFFICE
CERTIFICATE OF CORRECTION

PATENT NO. : 5,123,920
DATED : June 23, 1992
INVENTOR(S) : Bokros, Jack C.

It is certified that error appears in the above-indentified patent and that said Letters Patent is hereby corrected as shown below:

Col. 6, line 5, "surface" should be
--surfaces--. Column 6, line 40, "1" should be --1°--.
Column 7, line 35, "The" should be --This--.

IN THE CLAIMS: Claim 10, column 12, line 20, "surfaces" should be --surface--. Claim 14, column 13, line 6, "siad" should be --said--.

Signed and Sealed this

Twenty-fourth Day of August, 1993

Attest:

BRUCE LEHMAN

Attesting Officer

Commissioner of Patents and Trademarks